United States Patent [19]

Eubanks et al.

[11] Patent Number: 4,605,784

[45] Date of Patent: Aug. 12, 1986

[54] PROCESS FOR THE PREPARATION OF ETHER-CONTAINING CHLORIDES

[75] Inventors: Robert J. I. Eubanks; James G. Pacifici, both of Batesville, Ark.

[73] Assignee: Eastman Kodak Company, Rochester, N.Y.

[21] Appl. No.: 756,565

[22] Filed: Jul. 18, 1985

Related U.S. Application Data

[63] Continuation of Ser. No. 682,823, Dec. 19, 1984, abandoned, which is a continuation of Ser. No. 536,112, Sep. 26, 1983, abandoned.

[51] Int. Cl.$^4$ .................... C07C 41/22; C07C 41/18
[52] U.S. Cl. .................... 568/614; 568/607; 568/610; 568/655; 568/649; 568/663; 568/681
[58] Field of Search ............... 568/614, 607, 610, 649, 568/676, 655, 681, 663

[56] References Cited

U.S. PATENT DOCUMENTS 2,817,686 12/1957 Cicero et al. .
3,061,552 10/1962 Schenck et al. .
3,992,432 11/1976 Napier et al. .

OTHER PUBLICATIONS

Schwartz et al., Surface Active Agents, vol. I (1949) Interscience Publishers Inc., New York, pp. 338, 513, 15–17.

*Primary Examiner*—Howard T. Mars
*Attorney, Agent, or Firm*—Clyde L. Tootle; Gary C. Bailey; D. B. Reece, III

[57] ABSTRACT

Disclosed is a process for the preparation of ether-containing chlorides by reacting an ether-alcohol, ether-glycol or ether-polyglycol with a chlorinating agent such as thionyl chloride in the presence of a catalytic amount of a quaternary ammonium salt, the reaction being conducted at a temperature of about 25° C. to about 90° C.

9 Claims, No Drawings

PROCESS FOR THE PREPARATION OF ETHER-CONTAINING CHLORIDES

This is a continuation of application Ser. No. 682,823 filed Dec. 19, 1984, which was a continuation of Ser. No. 536,112 filed Sept. 26, 1983, both now abandoned.

DESCRIPTION

BACKGROUND OF THE INVENTION

This invention concerns a process for the preparation of ether-containing chlorides of the general formula $$R^2(OR^3)_nCl \qquad \text{III}$$

which are known to be useful as solvents as well as in the preparation of polymers, pharmaceuticals, etc.

Various methods have been employed for the preparation of ether-containing chlorides. Some of these methods include the chloroethylation of dioxane disclosed in U.S. Pat. No. 2,383,091 and of polyoxyethylene diols disclosed in U.S. Pat. No. 2,352,745. Also, Teramura and Oda, Chemical Society of Japan, 54, 605 (1951), disclose the preparation of 1,2-bis(2-chloroethoxy)ethane by the copper catalyzed coupling of 2-chloroethyl-1-chloromethyl ether. G. F. Zellhoefer, in Industrial Engineering Chemistry 29, 548 (1937), discloses the preparation of this same dichloro-substituted ether from triethylene glycol and thionyl chloride. No details of the reaction or yields, however, are disclosed. U.S. Pat. No. 3,294,847 discloses the preparation of the desired ether-containing chlorides by the action of phosphorous trichloride on certain ether-alcohols, ether-glycols and polyglycols in the presence of hydrogen chloride.

Many of the existing methods for preparing ether-containing chlorides are not completely satisfactory due to low yields of the desired product obtained or because of undesired mixtures of by-products which accompany the formation of the product compound and which are difficult to separate by conventional methods.

It is known that ether linkages, in the presence of good nucleophiles such as alcohols, are particularly susceptible to cleavage by strong acids such as hydrogen chloride. It, therefore, is apparent that any process modifications which reduce this potential would be highly advantageous since higher yields and increased product purities can be expected where the potential for ether cleavage is reduced or eliminated.

An improved process has now been found whereby ether-containing chlorides can be obtained in high yield, up to about 94% of theory, in short reaction times, without high levels of undesired mixtures of by-products, and without high reaction temperatures. By the process of this invention hydroxy-containing compounds such as ether-alcohols, ether-glycols and ether-polyglycols are reacted with certain chlorinating agents in the presence of a catalytic amount of certain quaternary ammonium salts.

SUMMARY OF THE INVENTION

The present invention concerns the preparation of compounds of the formula $$R^2(OR^3)_nCl \qquad \text{III}$$

by contacting a chlorinating agent with a compound of the formula $$R^1(OR^3)_nOH \qquad \text{I}$$

in the presence of a catalytic amount of a quaternary ammonium salt of the formula $$R^7-\underset{\underset{R^6}{|}}{\overset{\overset{R^4}{|}}{N}}-R^5, X^- \qquad \text{II}$$

wherein
n is an integer of from 1 to 20,
$R^1$ is alkyl of from 1 to 8 carbon atoms, aryl of from 6 to 10 carbon atoms, alkylaryl of from 7 to 18 carbon atoms, arylalkyl of from 7 to 10 carbon atoms, $HOCH_2CH_2-$ or $ClCH_2CH_2-$;
$R^2$ is alkyl of from 1 to 8 carbon atoms, aryl of from 6 to 10 carbon atoms, alkylaryl of from 7 to 18 carbon atoms, arylalkyl of from 7 to 10 carbon atoms, or $ClCH_2CH_2-$, wherein said $R^1$ of the reactant corresponds to said $R^2$ of the product except that said $R^2$ is $ClCH_2CH_2-$ when $R^1$ is $HOCH_2CH_2-$;
$R^3$ is an alkylene radical of from 2 to 3 carbon atoms;
$R^4$, $R^5$, $R^6$, and $R^7$ are each independently selected from alkyl of from 1 to 18 carbon atoms, alkylaryl of from 7 to 18 carbon atoms, arylalkyl of from 7 to 18 carbon atoms, and aryl of from 6 to 18 carbon atoms and X is a halide, hydrogen sulfate or hydroxide anion;
the reaction being conducted at a temperature of about 25° to about 90° C.

DETAILED DESCRIPTION OF THE INVENTION

In accordance with the process of this invention quaternary ammonium salts of formula II defined above are employed to catalyze the reaction of a chlorinating agent with ether-containing hydroxy compounds of formula I above, hereinafter referred to as ether-glycol. The quaternary ammonium salts of this process generally are employed in a catalytic amount, that is, any amount which exhibits a favorable comparison in the reaction as compared to the use of the chlorinating agent alone. Typically this amount will be about 0.1 to about 5.0% by weight of the ether-glycol reactant. Preferred quaternary ammonium salts include tetraethylammonium chloride, tetraethylammonium bromide, tetraethylammonium hydroxide, benzyltriethylammonium chloride, benzyltriethylammonium hydroxide, benzyltriethylammonium bromide, and ethyltrimethylammonium chloride.

Stoichiometric quantities of ether-glycol and chlorinating agent are employed. If desired, a slight excess of chlorinating agent may be employed, generally up to about 10%.

The preferred chlorinating agents are phosphorous pentachloride, phosphorous oxychloride, and thionyl chloride with the latter being most preferred. The reaction process is conveniently carried out at moderate temperatures, generally at a range of about 25° C. to about 90° C. Temperatures within the range of about 50° C. to about 70° C. are preferred. The reaction is normally conducted at atmospheric pressure and may advantageously be conducted under a nitrogen sweep. This effectively allows degassing of strong acid such as HCl, in the case of thionyl chloride, generated in the process and which is a source of competing side reactions such as cleavage of the ether linkage and of unwanted by-products.

As stated previously $R^1$ corresponds to $R^2$ except when $R^1$ is $HOCH_2CH_2$— then $R^2$ is $ClCH_2CH_2$—. Typical embodiments of each of $R^1$ and $R^2$ include methyl, ethyl, propyl, butyl, pentyl, octyl, phenyl, naphthyl, methylphenyl, butylphenyl, octylphenyl, nonylphenyl, dodecylphenyl, dibutylphenyl, benzyl, phenylethyl, and chloroethyl. Exemplary alkylene radicals of $R^3$ of the formulae disclosed hereinabove are methylene and ethylene.

Unlike many prior art processes which require the presence of dimethylformamide (DMF) to achieve suitable results the process of this invention gives good results without the use of DMF.

While the process of this invention is normally carried out by adding the chlorinating agent to a reaction mixture of the ether-glycol and quaternary ammonium salt, equally good results may be achieved by adding the ether-glycol to a reaction mixture of chlorinating agent and the catalyst. The rate of addition of chlorinating agent can be widely varied but generally should be a sufficient rate to utilize the chlorinating agent efficiently. On a laboratory scale, such as disclosed in the experimental examples set out hereinbelow, addition of thionyl chloride was complete in about two hours. Of course, the time can be expected to vary depending on such things as the size of the reaction, the reaction conditions, the reactants, the equipment used, etc. During the addition of the thionyl chloride in the experimental examples which follow hydrogen chloride and sulfur dioxide gases are evolved, thereby minimizing harsh strong acid reaction conditions. After addition of the thionyl chloride the reaction mixture is held at the same temperature (25° C.–90° C.) for a period of time sufficient to ensure completion of the reaction. About 0.25 to 1.0 hour on a small laboratory scale normally is sufficient. Any unreacted thionyl chloride which may be present is then removed, i.e. by vacuum distillation, and the product readily isolated by cooling the reaction mixture to room temperature. The resulting product is obtained in good yield (up to about 94% for 1,2-bis(2-chloroethoxy)ethane) and purity and can be used without further purification.

The process of this invention can be carried out in the presence or absence of a solvent, depending on the reactant employed. For example, ether-containing alcohols having high melting points can be chlorinated in solvents such as heptane or toluene. Removal of the solvent may then be achieved by conventional stripping methods when the circumstances require.

By the process of this invention the desired ether-containing chloride product is obtained in good yield and purity without the use of long reaction times, large excesses of chlorinating agent or elevated reaction temperatures.

The following examples are given to further illustrate the invention, but it is to be understood that the invention is not to be limited in any way by the details described therein.

EXPERIMENTAL EXAMPLE 1

Preparation of 1,2-Bis(2-Chloroethoxy)ethane Using Benzyltriethylammonium Chloride as Catalyst A mixture of triethylene glycol (0.5 mole) and benzyltriethylammonium chloride (0.0018 mole) was heated to and maintained at 60° to 65° C. while thionyl chloride (1.1 mole) was added over a two-hour period. After the addition was completed, the batch was held at 60° C. to 65° C. for one hour. Unreacted thionyl chloride was removed by distillation at reduced pressure (ca 200 mm) to a pot temperature of 85° to 90° C. The product was cooled to room temperature and stored. Approximately 93.7 grams of a clear, pale yellow liquid was isolated which assayed 95.6 percent by GC (0.474 mole, 94.7 percent of theory). The IR and NMR(H) matched those of authentic material.

EXPERIMENTAL EXAMPLE 2

Preparation of 1,2-Bis(2-Chloroethoxy)ethane in the Absence of a Quaternary Ammonium Salt as Catalyst The experimental procedure of Example 1 was repeated but in the absence of benzyltriethylammonium chloride. Approximately 96.0 grams of a dark brown liquid was isolated which assayed 62.9 percent by GC (0.319 mole, 63.9 percent of theory). The IR and NMR(H) spectra did not match those of authentic material.

EXPERIMENTAL EXAMPLE 3

Preparation of 1,2-Bis(2-Chloroethoxy)ethane Using Benzyltriethylammonium Chloride as Catalyst Demonstrating the Effectiveness of the Process Wherein the Ether-Glycol is Added to a Reaction Mixture of Thionyl Chloride and Catalyst A mixture of thionyl chloride (1.1 mole) and benzyltriethylammonium chloride (0.0025 mole) was heated to and maintained at 30° to 35° C. while triethylene glycol (0.5 mole) was added over a one-hour period. After the addition was completed, the bath was allowed to stand while degassing of HCl and $SO_2$ occurred. Unreacted thionyl chloride was removed by distillation at reduced pressure (ca. 20 mm.) to a pot temperature of 80° to 90° C. Total product isolated was 91.4 g. which assayed 94.8 percent (91.7% of theory).

The invention has been described in detail with particular reference to preferred embodiments thereof, but it will be understood that variations and modifications can be effected within the spirit and scope of the invention.

We claim:

1. A process for the preparation of a compound having the formula $$R^2(OR^3)_nCl \qquad \qquad III$$

by contacting a chlorinating agent selected from the group consisting of phosphorous pentachloride, phosphorous oxychloride and thionyl chloride with a compound of the formula $$R^1(OR^3)_nOH \qquad \qquad I$$

in the presence of a catalytic amount of a quaternary ammonium salt of the formula $$\begin{array}{c} R^4 \\ | \\ R^7-N-R^5, X^- \\ | \\ R^6 \end{array} \qquad \qquad II$$

wherein
n is an integer of from 1 to 20, $R^1$ is alkyl of from 1 to 8 carbon atoms, aryl of from 6 to 10 carbon atoms, alkylaryl of from 7 to 18 carbon atoms, arylalkyl of from 7 to 10 carbon atoms, $HOCH_2CH_2-$ or $ClCH_2CH_2-$;

$R^2$ is alkyl of from 1 to 8 carbon atoms, aryl of from 6 to 10 carbon atoms, alkylaryl of from 7 to 18 carbon atoms, arylalkyl of from 7 to 10 carbon atoms, or $ClCH_2CH_2-$, wherein said $R^1$ of the reactant corresponds to said $R^2$ of the product except that said $R^2$ is $ClCH_2CH_2-$ when $R^1$ is $HOCH_2CH_2-$;

$R^3$ is an alkylene radical of from 2 to 3 carbon atoms;

$R^4$, $R^5$, $R^6$, and $R^7$ are each independently selected from alkyl of from 1 to 18 carbon atoms, alkylaryl of from 7 to 18 carbon atoms, arylalkyl of from 7 to 18 carbon atoms, and aryl of from 6 to 18 carbon atoms and X is a halide, hydrogen sulfate or hydroxide anion;

the reaction being conducted at a temperature of about 25° to about 90° C.

2. A process according to claim 1 wherein the quaternary ammonium salt is employed in an amount of about 0.1 to about 5.0% by weight of the ether-containing reactant.

3. A process according to claim 1 wherein the chlorinating agent is thionyl chloride and is employed in a stoichiometric amount.

4. A process according to claim 1 wherein the contacting is carried out at a temperature range of about 50° C. to about 70° C.

5. A process according to claim 1 wherein $R^3$ is ethylene.

6. A process according to claim 1 wherein the ether-containing glycol reactant is triethylene glycol.

7. A process according to claim 1 wherein the quaternary ammonium salt is selected from the group consisting of tetraethylammonium chloride, tetraethylammonium bromide, tetraethylammonium hydroxide, benzyltriethylammonium chloride, benzyltriethylammonium hydroxide, benzyltriethylammonium bromide, and ethyltrimethylammonium chloride.

8. A process according to claim 1 wherein the quaternary ammonium salt is benzyltriethyl ammonium chloride.

9. A process according to claim 9 wherein the quaternary ammonium salt is present in an amount of about 0.1 to 5.0% by weight of compound I.

* * * * *